(12) United States Patent
Gurjar et al.

(10) Patent No.: US 6,713,639 B1
(45) Date of Patent: Mar. 30, 2004

(54) PROCESS FOR PREPARING ENANTIOMERICALLY PURE (S)-3-HYDROXY-GAMMA-BUTYROLACTONE

(75) Inventors: Mukund Keshao Gurjar, Pune (IN); Pradeep Kumar, Pune (IN); Anis Naim Deshmukh, Pune (IN); Rajesh Kumar Upadhyay, Pune (IN); Puspesh Kumar Upadhyay, Pune (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/281,615

(22) Filed: Oct. 28, 2002

(51) Int. Cl.⁷ .............................. C07D 307/20

(52) U.S. Cl. ...................................... 549/313

(58) Field of Search ........................ 548/313

(56) References Cited

U.S. PATENT DOCUMENTS

| | | | | |
|---|---|---|---|---|
| 4,138,484 A | 2/1979 | Fuxe | ............ | 424/247 |
| 5,292,939 A | 3/1994 | Hollingsworth | ............ | 562/515 |
| 5,319,110 A | 6/1994 | Hollingsworth | ............ | 549/313 |
| 5,374,773 A | 12/1994 | Hollingsworth | ............ | 562/515 |
| 6,288,272 B1 | 9/2001 | Roh et al. | ............ | 562/515 |

FOREIGN PATENT DOCUMENTS

| | | |
|---|---|---|
| EP | 0452143 | 10/1991 |
| WO | 9405639 | 3/1994 |
| WO | 9804543 | 2/1998 |
| WO | 9905092 | 2/1999 |

OTHER PUBLICATIONS

Hollingsworth, "Taming Carbohydrate Complexity, etc" J. Org. Chem. 1999, 64, 7633–7634.*

Rumin et al., (1995) "Novel Ligand Transformations in Cluster Complexes. Activation of C–F Bonds in a Perfluorovinyldiiron(1) Complex by Primary and Secondary Amines", J. Chem. Soc., Chem. Commun., pp. 1431–1432.

Kim et al., (1995) "Crystal Structure of HIV–1 Protease in Complex with VX–478, a Potent and Orally Bioavailable Inhibitor of the Enzyme", J. Am. Chem. Soc. 117, pp. 1181–1182.

(List continued on next page.)

*Primary Examiner*—Patricia L. Morris
(74) *Attorney, Agent, or Firm*—Baker Botts LLP

(57) ABSTRACT

The present invention relates to a process for the in situ preparation of optically pure (S)-3,4-dihydroxybutyric acid derivatives represented by the Formula [2] and more particularly, to a process which enables preparing optically pure (S)-3-hydroxy-γ-butyrolactone represented by Formula [1] by oxidation of α- or β-(1,4) linked disaccharide or oligosaccharide with an oxidant under basic condition to give acid and cyclization sequentially under acidic condition to give (S)-3-hydroxy-γ-butyrolactone.

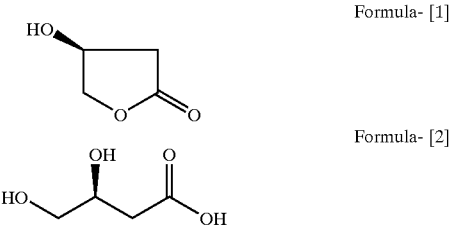

21 Claims, 1 Drawing Sheet

OTHER PUBLICATIONS

Brower et al., (1992) "The Synthesis of (4R–cis)–1,1–Dimethylethyl 6–cyanomethyl–2,2–dimethyl–1,3–dioxane–4–acetate, a Key Intermediate for the Preparation of CI–981, a Highly Potent, Tissue Selective Inhibitor of HMG–CoA Reductase", Tetrahedron Letters, vol. 33, pp. 2279–2282.

Ahn et al., (1992) "Syntheses of 1–Oxaquinolizidines Via Reductive Cyclization of Hydroxy–Lactams", Tetrahedron Letters, vol. 33, pp. 507–510.

Verhaar et al., (1991) "High–performance liquid chromatography of reaction mixtures from the oxidation and degradation of lactose", journal of ChHromatography, 549: pp. 113–125.

Arts et al., (1996) "Hydrogen Peroxide and Oxygen in Catalytic Oxidation of Carbohydrates and Related Compounds", Synthesis, pp. 597–613.

Larchevêque et al., (1990) "Enantiomerically pure β,γ–epoxyesters from β–hydroxylactones: synthesis of β–hydroxyesters and (–)–GABOB", Tetrahedron, vol. 46: pp. 4277–4282.

Nakamura et al., (1990) "A Novel Method to synthesize (L)–β–Hydroxyl Esters By The Reduction With Bakers Yeast", Tetrahedron Letters, vol. 31: pp. 267–270.

Uchikawa et al., (1988) "Synthesis of (S)–and (R)–3–Hydroxy–4–butanolide and (2S,4S)–, (2R,4S)–, (2S,4R)–, and (2R,4R)–2–Hydroxy–4–hydroxymethyl–4–butanolide and Their Satiety and Hunger Modulating Activities", Bull. Chem. Soc. Jpn., 61: pp. 2025–2029.

Hanessian et al., (1987) "A synthetic strategy for tricholomic acid and acivicin", Can. J. Chem., 65: pp. 195–199.

Papageorgiou et al., (1985) "Use of Enzymatic Hydrolysis of Dimethyl Malates for a Short Synthesis of Tulipalin B and of Its Enantiomer", J. Org. Chem., 50: p. 1144–1145.

Saito et al., (1984) "Combination of Borane–Dimethyl Sulfide Complex with Catalytic Sodium Tetrahydroborate as a Selective Reducing Agent For a α–Hydroxy Esters: Versatile Chiral Building Block From (S)–(–)–Malic Acid", Chemistry Letters, pp. 1389–1392.

John W. Green (1955) "The Effect of Alkali on Carboxydrates. I. Saccharinic Anilides Derived from D–Glucose, L–Arabinose and Cellobiose", J. Am. Chem. Soc., 78: pp. 1894–1897.

Magnusson et al., (1952) "Stabilities of +4 and +5 Oxidation States of the Actinide Elements—the Np(IV)–Np(V) Couple in Perchloric Acid Solution", J. Am. Chem. Soc., 75: pp. 2242–2248.

Rowell et al., (1969) "Oxidative Alkaline Degradation of Cellobiose", Carboxydrate Res., 11: pp. 17–25.

Whistler et al., (1958) "Oxiadtion of Amylopectin with Hydrogen Peroxide at Different Hydrogen Ion Concentrations", J. Am. Chem. Soc., 81: pp. 3136–3139.

Hollingsworth, (1999) "Taming carbohydrate complexity: A facile, high yield route to chiral 2,3–dihydroxybutanoic acids and 4–hydroxytetrahydrofuran–2–ones with very high optical purity from pentose sugars," J. Org. Chem. 64: pp. 7633–7634.

* cited by examiner

PROCESS FOR PREPARING ENANTIOMERICALLY PURE (S)-3-HYDROXY-GAMMA-BUTYROLACTONE

The present invention relates to a process for the in situ preparation of optically pure (S)-3,4-dihydroxybutyric acid derivatives represented by Formula [2] below and more particularly, to a process which enables preparing optically pure (S)-3-hydroxy-γ-butyrolactone represented by Formula [1] below by oxidation of an α- or β-(1,4) linked disaccharide or oligosaccharide with an oxidant under basic conditions to give acid and cyclization sequentially under acidic condition to give (S)-3-hydroxy-γ-butyrolactone.

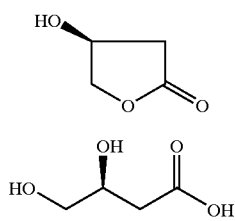

Formula [1]

Formula [2]

BACKGROUND AND PRIOR ART OF THE PRESENT INVENTION (S)-3-Hydroxy-γ-butyrolactone (HGB) is an important synthetic intermediate for variety of chiral compounds. It is a key intermediate for preparing (R)-GABOB, gamma-amino beta-hydroxybutyric acid, a neuromediater (Tetrahedron 1990, 46, 4277); L-carnitine, a health supported agent (WO 99/05092); atorvastatin, a HMG-CoA reductase inhibitor which is used as a cholesterol lowering drug (Tetrahedron Lett., 1992, 33, 2279); and (S)-3-tetrahydrofuran, an AIDS drug intermediate (J. Am. Chem. Soc. 1995, 117, 1181; WO 94/05639). (S)-3-Hydroxy-γ-butyrolactone has been reported as a satiety agent (Okukado et al. Bull. Chem. Soc. Jpn 1988. 61, 2025) as well as a potentiating agent to neuroleptic drugs (U.S. Pat. No. 4,138,484.) It is also useful intermediate in synthetic efforts towards natural products. (J. Org. Chem. 1985, 50, 1144, Can. J. Chem. 1987, 65, 195, Tetrahedron Lett.1992, 507.) HGB serves as an important precursor for the production of a variety of natural and clinical products.

The present invention relates to a new method of producing secondary chiral feedstock, (S)-3-hydroxy-γ-butyrolactone (HGB), from lactose, maltose and maltodextrin. This approach can be used in the efficient synthesis of members of a large family of chiral intermediates without the need to design custom chiral synthesis for each new compound. The method provides a cost-effective method of producing pure (S)-3-hydroxy-γ-butyrolactone at the process level.

The prior art shows that synthesis of (S)-3-hydroxy-γ-butyrolactone has been accomplished employing various strategies. A commonly used strategy for the synthesis of a compound-represented by Formula [1] and its intermediate (S)-3-hydroxybutyric acid derivatives is from the enzymatic or catalytic reduction of β-keto ester (EP452143A2, Tetrahedron Lett. 1990, 31, 267; J. Am. Chem. Soc. 1983, 105, 5935).

(S)-3-hydroxy-γ-butyrolactone can also be obtained from the selective reduction of (L)-malic acid ester (U.S. Pat. No. 5,808,107, Chem. Lett. 1984, 1389).

The treatment of a carbohydrate containing a glucose substituent in the 4-position, such as cellobiose (β-1,4-linked glucose disaccharide), maltose (the α-1,4 linked isomer, amylose and cellulose with alkali, has been shown to produce a low yield of the desired material, along with D, L-2,4-dihydroxybutyric acid, glycolic acid isosaccharinic acid, ketones, diketones, glycolic acid and a plethora of other degradation and condensation products (Corbett et al. J. Chem. Soc. 1995, 1431; Green, J. W. J. Am. Chem. Soc. 1956, 78, 1894, Rowell, R. M. et al Carbohydrate Res.1969, 11, 17).

(S)-3,4-dihydroxybutyric acid was also obtained as a major product by alkaline degradation of carbohydrates to give the dicarbonyl compound and subsequent reaction with hydrogen peroxide (J. Chem. Soc. 1960, 1932).

(S)-3,4-dihydroxybutyric acid was obtained from lactose using a base and an oxidant. The acid obtained was cyclized to (S)-3-hydroxy-γ-butyrolactone and purified by protection of the two hydroxyl groups to acetonide ester compound, methyl (S)-3,4-O-isopropylidene-3,4-dihydroxybutanoate which was recyclized to (S)-3-hydroxy-γ-butyrolactone under acidic media (WO 98/04543).

A large number of methods have been developed to make (S)-3,4-dihydroxybutyric acid by alkaline oxidation of carbohydrate containing glucose substituent at the 4-position (U.S. Pat. Nos. 5,292,939, 5,319,110 and 5,374,773). In these methods, the dicarbonyl compounds formed is oxidized to (S)-3,4-dihydroxybutyric acid and glycolic acid.

(S)-3,4-dihydroxybutyric acid has also been prepared from carbohydrates either using base only or using oxygen in base. The yield reported of the desired compound is very low (30%) due the formation of large number of by-products (J. Am. Chem. Soc. 1953, 2245, J. Am. Chem. Soc. 1955, 1431, Carbohydrate Res. 1969, 11, 17, J. Chromatography 1991, 549, 113).

(S)-3,4-dihydroxybutyric acid has been prepared by alkaline oxidative degradation of polysaccharides such as maltodextrin, starch and cellulose with (1,4) and/or (1,6) linked glucose units. The reaction leads to the complex mixture containing formic acid, oxalic acid, glycolic acid and erythronic acid (J. Am. Chem. Soc.1959, 81, 3136, Synthesis 1997, 597).

(S)-3,4-dihydroxybutyric acid derivatives has been prepared by oxidation of α-(1,4) linked oligosaccharides with a basic anion exchange resin with an oxidants to give (S)-3, 4-dihydroxybutyric acid anion exchange resin complex dissociating the (S)-3,4-dihydroxybutyric acid from anion exchange resin complex.

Chiral dihydroxybutyric acids and the corresponding esters, lactones and derivatives have proven to be valuable chemical entities. (S)-3-Hydroxy-γ-butyrolactone (HGB) is an important building block to produce other chiral intermediates using classical chemistry methodology. Defunctionalization of carbohydrate has been attracting much attention as a vibrant synthetic tool for the enantioselective synthesis of a variety of compounds. The synthesis of a chiral compound with desired number of chiral centers could be achieved by eliminating the unneeded chiral centers quickly from carbohydrate precursors. A large number of a small-scale complex synthesis of (S)-3-hydroxy-γ-butyrolactone have been reported demonstrating the value of this compound. Therefore, there is a genuine need for simple and inexpensive method for the large-scale preparation of (S)-3-hydroxy-γ-butyrolactone and its derivatives.

The methods in the prior-art are described above and found in Table 1 below. These methods have shown that expensive metal catalysts are used for the reduction of the prochiral center, e.g. enzymatic or catalytic reduction of β-keto ester. Furthermore, selective reduction to only one of the two functional groups is achieved. In addition, the yields of (S)-3,4-dihydroxybutyric acid and (S)-3-hydroxy-γ-butyrolactone produced have been low and (S)-3,4- dihydroxybutyric acid can be overoxidized to formic acid and glycolic acid.

Many methods are not suitable as low yield of the desired product is obtained due to the formation of large number of side product such as glycolic acid, isosaccharinic acid, formic acid, ketone, diketone and glycolic acid. The optical purity of the compound is low, having poor enantioselectivity.

Purification of the target compound, (S)-3-hydroxy-γ-butyrolactone, can be difficult due to the formation of a complex mixture, containing formic acid, oxalic acid, glycolic acid and erythronic acid. The prior art methods require a multi-step synthesis, long reaction times, high reaction temperatures, and produce an overall low yield of the desired compound.

In view of the above-mentioned disadvantages of the prior-art procedures, it is desirable to develop an efficient and enantioselective process for the synthesis of (S)-3-hydroxy-γ-butyrolactone, which overcomes the drawbacks of the prior art process employing the oxidation of a D-hexose source under basic condition.

TABLE 1

Comparison of Prior Art Methods

| Process | Starting material | No. of steps | Optical purity (ee) | Yield |
|---|---|---|---|---|
| U.S. Pat. No. 6,288,272 | Amylopectin Method (enzymatic reaction) | Four steps | From disaccharide Maltose (94%) From oligosaccharide (99.9%) | 20.2 to 23.7 Wt. % |
| U.S. Pat. No. 5,292,939 | Starch, Maltose (Oxidizing agent, $H_2O_2$) | Two | Not mentioned | 66–85% |
| WO 04543 (1998) | Lactose | Four steps | Not mentioned | Not mentioned |
| Synthesis, 570, (1987) | D-isoascorbic acid | Seven steps | Not mentioned | 88% |
| Syn. Commun. 16,183 (1986) | (S)-Aspartic acid | Four steps | 94–97% | 83% |

The present invention provides a method for synthesizing (S)-3-hydroxy-γ-butyrolactone by using inexpensive, readily available carbohydrate material, such as maltose, maltodextrin and lactose. A carbohydrate source is treated in a solvent with cumene hydroperoxide in the presence of a base, which leads to the formation of (S)-3,4-dihydroxybutyric acid and glycolic acid. The subsequent acidification with an acid and removal of solvent affords the desired (S)-3-hydroxy-γ-butyrolactone in optically active form. Thus employing the secondary chiral feedstock strategy, the readily available natural raw material could be used to manufacture (S)-3-hydroxy-γ-butyrolactone (HGB) which act as a building block for a wide range of products. The new technology offers a practical and cost-effective route and would have an advantage since it avoids use of expensive starting material to make the (S)-3-hydroxyl-γ-butyrolactone.

SUMMARY OF THE PRESENT INVENTION

The present invention provides a process for preparing enantiomerically pure (S)-3-hydroxy-γ-butyrolactone. The process provided herein is a simple, inexpensive and economical method of preparing enantiomerically pure (S)-3-hydroxy-γ-butyrolactone.

Accordingly, the present invention provides a process for the preparation of enantiomerically pure (S)-3-hydroxy-γ-butyrolactone by dissolving D-hexose source in an aqueous alkali solution, heating the solution to a temperature in the range of 40° C. to 50° C. for a period of 1 to 4 hours, adding a peroxide reagent raising the temp of the reaction mixture up to 70° C., cooling the reaction mixture to about 25° C. and acidifying to about pH 1.0, evaporating the acidified solution to dryness to remove water and glycolic acid to obtain a yellow syrup, neutralizing the yellow syrup with solid alkali carbonate, extracting with an organic solvent, drying the organic layer over anhydrous sodium sulfate, evaporating the filtrate to obtain a residue and purifying the residue over silica gel column using a mixture of organic solvent as an eluant to obtain the pure compound (S)-3-hydroxy-γ-butyrolactone.

DETAILED DESCRIPTION OF THE PRESENT INVENTION

Figure 1:
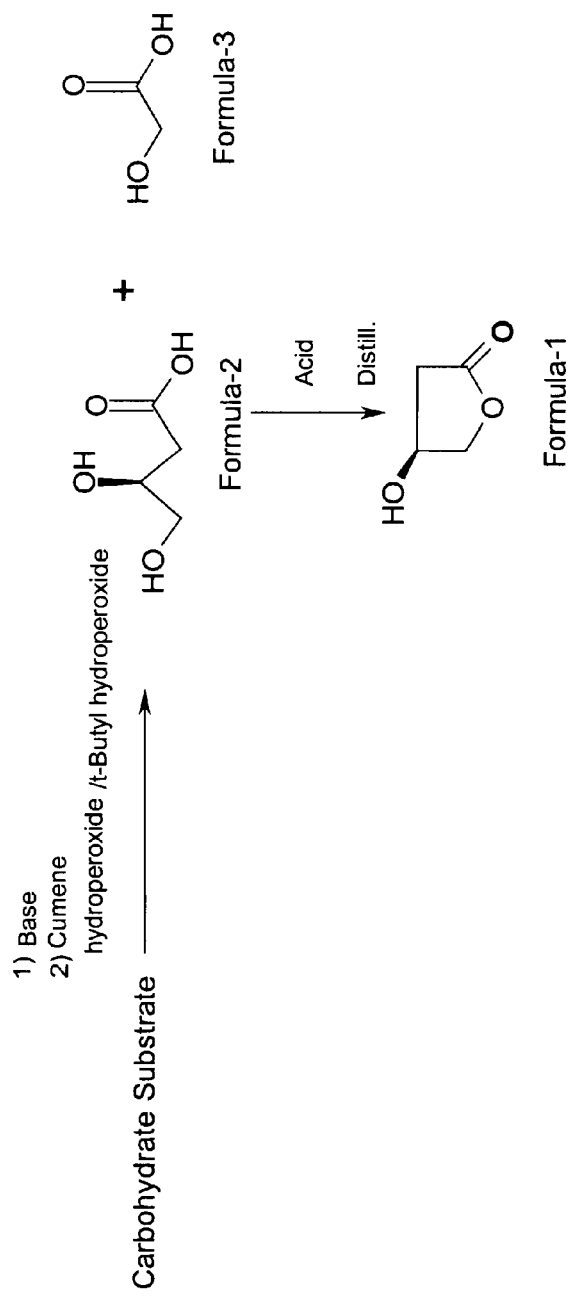
FIG. 1 shows a schematic of the process of the present invention.

The present invention provides a process for the preparation of enantiomerically pure (S)-3-hydroxy-γ-butyrolactone said process comprising
(i) dissolving a D-hexose source in an aqueous alkali solution,
(ii) heating the solution to a temperature in the range of 40° C. to 50° C. for a period of 1 to 4 hours to obtain a dark yellow to dark red color solution,
(iii) adding a peroxide reagent to the solution,
(iv) raising the temperature of the solution to about 70° C. for 8 to 24 hours to obtain a reaction mixture of 3,4-dihydroxybutyric acid (2) and glycolic acid of (3),
(v) cooling the reaction mixture to a temperature of about 25° C.,
(vi) adding an acid to the reaction mixture to about pH 1.0,
(vii) evaporating the reaction mixture of step (vi) to dryness to remove water and glycolic acid (3) to obtain a yellow syrup,
(viii) neutralizing the yellow syrup with solid base,
(ix) extracting with an organic solvent,
(x) drying the organic layer over anhydrous sodium sulfate to obtain a residue, and
(xi) purifying the residue over a silica gel column using a mixture of organic solvent as an eluant to obtain the pure compound (S)-3-hydroxy-γ-butyrolactone.

One embodiment of the invention provides a process, wherein the base used in step (i) is derived from an alkali or an alkaline earth metal preferably an alkali metal hydroxide.

In another embodiment of the invention, the oxidizing agent is selected from the group consisting of cumene hydroperoxide, and tertiary butyl hydroperoxide, with cumene hydroperoxide being preferred.

In another embodiment, the molar concentration of base used is in the range of about 0.005M–0.2M and the oxidizing agent used is in the range between about 0.001M and 0.2M.

In yet another embodiment of the invention provides a process, wherein the D-hexose source used in step (i) is selected from the group consisting of maltose, lactose, and maltodextrin; preferably maltose and maltodextrin.

In yet another embodiment, the D-hexose source is selected from the group consisting of glucose, and galactose attached to the glucose substituents in the 4-position and preferably glucose or galactose.

In yet another embodiment, the reaction temperature in step (iv) is preferably between about 25° C. and 70° C. for 10–24 hours.

In another embodiment, the base used in step (viii) for neutralization is selected from the group consisting of sodium hydroxide, sodium bicarbonate, and sodium carbonate with sodium bicarbonate being preferred.

In another embodiment, the solvent used in step (ix) for the extraction is selected from ethyl acetate, chloroform and ether, preferably ethyl acetate.

In another embodiment, the eluant used in step (xii) for purification is mixture of solvent selected from the group consisting of pet ether, ethyl acetate, chloroform, methanol, and mixtures thereof; preferably a mixture of ethyl acetate and pet ether.

In yet another embodiment, the acid used for cyclization of the 3,4 dihydroxybutyric acid is a protic acid selected from the group consisting of HCl, $H_2SO_4$, methanesulfonic acid, and trifluoromethanesulfonic acid; preferably HCl or $H_2SO_4$.

In yet another embodiment, the 3-hydroxy-γ-butyrolactone obtained in step (xi) is (S)-3-hydroxy-γ-butyrolactone.

The process of the present invention is shown in FIG. 1.

One more embodiment of the present invention provides an improved, efficient and practical process for the synthesis of (S)-3-hydroxy-γ-butyrolactone, which comprises 1) treating the D-hexose source with a base and peroxide as oxidizing agent at 25° C. to 70° C. temperature to obtain 3,4-dihydroxybutyric acid of Formula[2] and glycolic acid of Formula [3], and ii) treating 3,4-dihydroxybutyric acid with an acid, removing water and glycolic acid under rotary evaporation and extracting the residue with an organic solvent after neutralization with a base and purifying it by column chromatography using mixture of organic solvents as eluant to obtain compound of Formula [1].

The present invention possesses several significant features over the prior art. The process is simple, inexpensive and economical. Synthesis of the desired compound requires only a single step process. The method produces an optically pure compound. The process provides a compound that has high enantioselectivity. The process leads to moderate to good yields of the desired compound. Furthermore, the carbohydrate source used in the process is cheap and readily available, making the process economical. Another noteworthy feature of the present invention is that both enantiomers could be prepared using this process.

Unlike other conventional oxidizing agents, the cumune hydroperoxide preferably used in the reaction is stable under alkaline conditions for longer duration of time, thus making the process more efficient. In addition, the reaction temperature is lower than prior art methods of synthesis.

EXAMPLES

The process of the present invention is further illustrated by the following examples, which may not however be construed to limit the scope of present invention. Table 2 shows a comparison of the compounds produced from Examples 1–5.

Example 1

In a two-necked 100 mL round bottom flask with thermo well and reflux condenser, was added maltose monohydrate (1.0 g, 2.77 mmol) dissolved in 0.16 M NaOH solution (0.32 g in 50 mL water, 7.93 mmol, 2.86 eq.). The reaction mixture was heated at 40° C., for 2 h. The color of the reaction mixture became dark yellowish to dark red. To this solution, 80% cumene hydroperoxide (0.68 mL~1.0 mL, 3.66 mmol, 1.32 eq.) was added slowly.

The reaction temperature was increased slowly to 70° C. and heated at this temperature for another 8 hours. The reaction mixture was cooled to 25° C. and then to 0° C. temperature. The cooled reaction mixture was acidified with conc. $H_2SO_4$ to pH 1 using a pH-meter. The acidified solution was concentrated to dryness at 50° C., on rotavapour in order to remove glycolic acid and water. To the yellow colored syrup formed, 5 g of ice was added. The syrup mixture was neutralized with solid sodium bicarbonate, extracted with ethyl acetate and dried over sodium sulfate. The solvent was removed under reduced pressure. The residue obtained was purified by silica gel column using eluant, EtOAc:Pet ether (4:6), to give the pure product having an optical purity of 94% (0.153 g), i.e. 54% yield.

Example 2

In a two-necked 100 mL round bottom flask with thermo well and reflux condenser, was added maltodextrin (1.0 g, 2.77 mmol) dissolved in 0.16 M KOH solution (0.32 g in 50 mL water, 7.93 mmol, 2.86 eq.). The reaction mixture was heated at 40° C. for 2 h. The color of the reaction mixture became dark yellowish to dark red. To this solution, 80% cumene hydroperoxide (0.68 mL~1.0 mL, 3.66 mmol, 1.32 eq) was added slowly. The reaction temperature was increased slowly to 70° C. and heated for another 8 h.

The reaction mixture was cooled to 25° C., and then to 0° C. temperature. The cooled reaction mixture was acidified with conc. $H_2SO_4$ to pH 1 using a pH-meter. The acidified solution was concentrated to dryness at 55° C., on rotavapour in order to remove glycolic acid and water. To the yellow colored syrup formed, 10 g of ice was added. The syrup mixture was neutralized with solid sodium bicarbonate, extracted with ethyl acetate and dried over sodium sulfate. The solvent was removed under reduced pressure. The residue obtained was purified by silica gel column using eluant EtOAc:Pet ether (4:6) to give the pure product with optical purity of 90% (0.16 g), i.e. 56% yield.

Example 3

In a two necked 100 ml round bottom flask with thermowell and reflux condenser, was added lactose (1.0 gm, 2.77 mmol) dissolved in 0.16 M NaOH solution (0.32 gm in 50 ml water, 7.93 mmols, 2.86 eq.). The reaction mixture was heated at 40° C. for 2 h. The color of the reaction mixture became dark yellowish to dark red. To this solution, 80% cumene hydroperoxide (0.68 ml~1.0 mL. 3.66 mmol, 1.32 eq.) was added slowly. The reaction temperature was increased slowly to 70° C. and heated for another 10 h.

The reaction mixture was cooled to 25° C., and then to 0° C. temperature. The cooled reaction mixture was acidified with conc. HCl to pH 1.0 using a pH-meter. The acidified solution was concentrated to dryness at 60° C. on rotavapour in order to remove glycolic acid and water. To the yellow colored syrup formed, 10 g of ice was added. The syrup mixture was neutralized with solid sodium bicarbonate, extracted with ethyl acetate and dried over sodium sulfate. The solvent was removed under reduced pressure. The residue obtained was purified by silica gel column using eluant EtOAc:Pet ether (4:6) to give the pure product with optical purity of 88% (0.107 g), i.e. 38% yield.

Example 4

In a two-necked 100 ml round bottom flask with thermo well and reflux condenser, was added maltose (1.0 g, 2.77 mmols) dissolved in 0.16 M NaOH solution (0.32 g in 50 mL water, 7.93 mmol, 2.86 eq.). The reaction mixture was heated at 40° C. for 2 h. The color of the reaction mixture became dark yellowish to dark red. To this solution, 70% tertiary butyl hydrogen peroxide (TBHP) (0.68 mL~1.0 mL., 3.66 mmols, 1.32 eq.) was added slowly. The reaction temperature was increased slowly to 70° C. and heated for another 8 h.

The reaction mixture was cooled to 25° C., and then to 0° C. temperature. The cooled reaction mixture was acidified with conc. H$_2$SO$_4$ to pH 1.0 using a pH-meter. The acidified solution was concentrated to dryness at 60° C. on rotavapour in order to remove glycolic acid and water. To yellow colored syrup formed, 10 g of ice was added. The syrup mixture was neutralized with solid sodium bicarbonate, extracted with chloroform and dried over sodium sulfate. The solvent was removed under reduced pressure. The residue obtained was purified by silica gel column using eluant EtOAc:Pet ether (4:6) to give the pure product with optical purity of 92% (0.098 g), i.e. 35% yield.

Example 5

In a two-necked 100 ml round bottom flask with thermowell and reflux condenser, was added maltose (1.0 g, 2.77 mmol) dissolved in 0.16M NaOH solution (0.32 g in 50 mL water, 7.93 mmols, 2.86 eq.). The reaction mixture was heated at 40° C. for 2 h. The color of the reaction mixture became dark yellowish to dark red. To this solution, 5-6M t-butyl hydroperoxide in decane (5.5 mL., 2.77 mmol, 1 eq.) was added slowly. The reaction temperature was increased slowly to 70° C. and heated for another 24 h.

The reaction mixture was cooled to 25° C., and then to 0° C. temperature. The cooled reaction mixture was acidified with conc. HCl to pH 1.0 using a pH-meter. The acidified solution was concentrated to dryness at 60° C. on rotavapour in order to remove glycolic acid and water. To the yellow colored syrup formed, 10 g of ice was added. The syrup mixture was neutralized with solid sodium carbonate, extracted with chloroform and dried over sodium sulfate. The solvent was removed under reduced pressure. The residue obtained was purified by silica gel column using eluant CHCl$_3$:MeOH (9:1) to give the pure product with optical purity of 94% (0.112 g), i.e. 39% yield.

TABLE 2

Yield of (S)-3-hydroxy-γ-butyrolactone products produced from Examples 1–5

| Example No. | Substrate | Oxidizing Agent Used | % Yield |
| --- | --- | --- | --- |
| 1 | Maltose | 80% Cumene hydroperoxide | 54% |
| 2 | Maltodextrin | 80% Cumene hydroperoxide | 56% |
| 3 | Lactose | 80% Cumen hydroperoxide | 38% |
| 4 | Maltose | 70% Tertiary butyl hydroperoxide (TBHP) | 35% |
| 5 | Maltose | 5–6M Tertiary butyl hydroperoxide in decane (TBHP) | 39% |

We claim:

1. A process for the preparation of enantiomerically pure (S)-3-hydroxy-γ-butyrolactone said process comprising
   (i) dissolving a D-hexose source in an aqueous alkali solution,
   (ii) heating the solution to a temperature in the range of 40° C. to 50° C. for a period of 1 to 4 hours to obtain a dark yellow to dark red color solution,
   (iii) adding a peroxide reagent to the solution,
   (iv) raising the temperature of the solution to about 70° C. for 8 to 24 hours to obtain a reaction mixture of 3,4-dihydroxybutyric acid and glycolic acid,
   (v) cooling the reaction mixture to a temperature of about 25° C.,
   (vi) adding an acid to the reaction mixture to about pH 1.0,
   (vii) evaporating the reaction mixture of step (vi) to dryness to remove water and glycolic acid to obtain a yellow syrup,
   (viii) neutralizing the yellow syrup with a solid base,
   (ix) extracting with an organic solvent,
   (x) drying the organic layer over anhydrous sodium sulfate to obtain a residue, and
   (xi) purifying the residue over a silica gel column using a mixture of organic solvents as an eluant to obtain the pure compound (S)-3-hydroxy-γ-butyrolactone.

2. The process of claim 1, wherein the aqueous alkali solution is derived from an alkali or an alkaline earth metal.

3. The process of claim 1, wherein the peroxide agent is selected from the group consisting of cumene hydroperoxide, tertiary butyl hydroperoxide, and cumene hydroperoxide.

4. The process of claim 1, wherein the molar concentration of the base is in the range of about 0.005M–0.2M and the peroxide agent is in the range between about 0.001M and 0.2M.

5. The process of claim 1, wherein the D-hexose source is a glucose source.

6. The process of claim 1, wherein the D-hexose source is selected from the group consisting of maltose, lactose, and maltodextrin.

7. The process of claim 5, wherein the glucose source is selected from the group consisting of glucose and galactose attached to the glucose substituent in the 4-position.

8. The process of claim 1, wherein the reaction temperature in step (iv) is between about 25° C. and 70° C. for 10–24 hours.

9. The process of claim 1, wherein the solid base for neutralization is selected from the group consisting of sodium hydroxide, sodium bicarbonate, and sodium carbonate.

10. The process of claim 1, wherein the organic solvent for extraction is selected from the group consisting of ethyl acetate, chloroform and ether.

11. The process of claim 1, wherein the eluant for purification is mixture of solvents selected from the group consisting of pet ether, ethyl acetate, chloroform, methanol, and mixtures thereof.

12. The process of claim 1, wherein the acid is a protic acid selected from the group consisting of HCl, H$_2$SO$_4$, methanesulfonic acid, trifluoromethanesulfonic acid.

13. The process of claim 1, wherein the 3-hydroxy-γ-butyrolactone is (S)-3-hydroxy-γ-butyrolactone.

14. The process of claim 2, wherein the aqueous alkali solution is an alkali metal hydroxide.

15. The process of claim 3, wherein the peroxide agent is cumene hydroperoxide.

16. The process of claim 6, wherein the D-hexose source is maltose.

17. The process of claim 6, wherein the D-hexose source is maltodextrin.

18. The process of claim 9, wherein in the solid base for neutralization is sodium bicarbonate.

19. The process of claim 11, wherein the organic solvent for extraction is a mixture of ethyl acetate and pet ether.

20. The process of claim 12, wherein the protic acid is HCl.

21. The process of claim 12, wherein the protic acid is H$_2$SO$_4$.

* * * * *